US012747470B2

(12) United States Patent
Yang et al.

(10) Patent No.: US 12,747,470 B2
(45) Date of Patent: Sep. 29, 2026

(54) METHOD AND SYSTEM FOR CONSTRUCTING SEQUENCING LIBRARY ON THE BASIS OF METHYLATED DNA TARGET REGION, AND USE THEREOF

(71) Applicant: MGI TECH CO., LTD., Shenzhen (CN)

(72) Inventors: Lin Yang, Shenzhen (CN); Yanyan Zhang, Shenzhen (CN); Qiwei Wang, Shenzhen (CN); Jia Lu, Shenzhen (CN); Fang Chen, Shenzhen (CN); Hui Jiang, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 1395 days.

(21) Appl. No.: 17/493,991

(22) Filed: Oct. 5, 2021

(65) Prior Publication Data

US 2022/0056519 A1 Feb. 24, 2022

Related U.S. Application Data

(63) Continuation of application No. PCT/CN2019/087824, filed on May 21, 2019.

(51) Int. Cl.
*C12Q 1/6869* (2018.01)
*C12N 15/10* (2006.01)
*C12Q 1/6806* (2018.01)

(52) U.S. Cl.
CPC ....... *C12Q 1/6869* (2013.01); *C12N 15/1093* (2013.01); *C12Q 1/6806* (2013.01);
(Continued)

(58) Field of Classification Search
None
See application file for complete search history.

(56) References Cited

U.S. PATENT DOCUMENTS

2014/0256563 A1 9/2014 Luo et al.
2015/0011396 A1 1/2015 Schroeder et al.
2019/0002872 A1 1/2019 Andersen et al.

FOREIGN PATENT DOCUMENTS

CN 105861724 A 8/2016
CN 106011230 A 10/2016
(Continued)

OTHER PUBLICATIONS

Adey et al. (Ultra-low-input, tagmentation-based whole-genome bisulfite sequencing, Genome Res., published Jun. 2012). (Year: 2012).*

(Continued)

*Primary Examiner* — Heather Calamita
*Assistant Examiner* — Elizabeth Rose Lafave
(74) *Attorney, Agent, or Firm* — Hodgson Russ LLP

(57) ABSTRACT

A method and system for constructing sequencing library, includes: obtaining a transformed DNA sample with a universal sequence; performing amplification using a first specific primer located upstream of the target region and a first universal primer at least partially matching or overlapping the universal sequence; and performing amplification using a second specific primer, a second universal primer and a tagged primer. The second specific primer is located downstream of the first specific primer and upstream of the target region, the second universal primer overlaps at least a partial sequence of the second specific primer, and the tagged primer overlaps a partial sequence of the first universal primer. Alternatively, the second specific primer is located downstream of the target region, the second universal primer overlaps at least a partial sequence of the first specific primer, and the tagged primer overlaps a partial sequence of the second specific primer.

6 Claims, 7 Drawing Sheets

Specification includes a Sequence Listing.

(52) U.S. Cl.
CPC . *C12Q 2523/125* (2013.01); *C12Q 2525/161* (2013.01); *C12Q 2525/179* (2013.01); *C12Q 2525/191* (2013.01); *C12Q 2535/122* (2013.01); *C12Q 2537/143* (2013.01); *C12Q 2563/179* (2013.01)

(56) References Cited

FOREIGN PATENT DOCUMENTS

| | | | | |
|---|---|---|---|---|
| CN | 107541791 | | 1/2018 | |
| CN | 107937985 | A | 4/2018 | |
| CN | 109666720 | | 4/2019 | |
| WO | 2018103025 | A1 | 6/2018 | |
| WO | WO-2018183723 | A1 * | 10/2018 | .......... B01F 33/3017 |

OTHER PUBLICATIONS

Taylor et al. (Construction of Effective Inverted Repeat Silencing Constructs Using Sodium Bisulfite Treatment Coupled with Strand-Specific PCR, BioTechniques, published 2012). (Year: 2012).*
Wen, Lu et al, "Genome-scale detection of hypermethylated CpG islands in circulating cell-free DNA of hepatocellular carcinoma patients", Cell Research, Oct. 30, 2015, pp. 1250-1264, vol. 25, Issue 11, Nature.
Varley, Katherine Elena et al., "Nested Patch PCR enables highly multiplexed mutation discovery in candidate genes", Genome Research, Oct. 10, 2008, pp. 1844-1850, vol. 18, Issue 11, Cold Spring Harbor Laboratory Press.
Vitak, Sarah A. et al., "Construction of thousands of single cell genome sequencing libraries using combinatorial indexing", bioRxiv preprint, Jul. 23, 2016, 18 pages, Cold Spring Harbor Laboratory Press.
Statham, Aaron L. et al., "Bisulfite sequencing of chromatin immunoprecipitated DNA (BisChIP-seq) directly informs methylation status of histone-modified DNA", Genome Research, Mar. 30, 2012, pp. 1120-1127, vol. 22, Issue 6, Cold Spring Harbor Laboratory Press.
EPO, Extended European Search Report for EP Appl. No. 19929647.6, Mar. 31, 2022.
WIPO, International Search Report for International Application No. PCT/CN2019/087824, Feb. 18, 2020.
Liu et al., "Recent Progress and Challenges in High Throughput RNA Methylation Sequencing Data Analysis," Progress in Biochemistry and Biophysics, 2015, vol. 42, No. 10.
CNIPA, First Office Action for CN Application No. 201980092935.8, Jun. 21, 2023.
JPO, Office Action for JP Application No. 2022-502317, Sep. 13, 2022.

* cited by examiner

SEQUENCE LISTING

```
<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: First specific primer

<400> SEQUENCE: 1

ggaggystag ygattttag                                    19


<210> SEQ ID NO 2
<211> LENGTH: 30
<212> TYPE: DNA
<213> ORGANISM: Artificial Sequence
<220> FEATURE:
<223> OTHER INFORMATION: First specific primer

<400> SEQUENCE: 2

gggagaattt tgaaaatgaa atatattttt                        30


<210> SEQ ID NO 3
<211> LENGTH: 24
<212> TYPE: DNA
<213> ORGANISM: Artificial Sequence
<220> FEATURE:
<223> OTHER INFORMATION: First specific primer
```

<400> SEQUENCE: 3
ttttygtttt tygttttygt tttt 24

<210> SEQ ID NO 4
<211> LENGTH: 23
<212> TYPE: DNA
<213> ORGANISM: Artificial Sequence
<220> FEATURE:
<223> OTHER INFORMATION: First specific primer

<400> SEQUENCE: 4
tttttgaatt ygaggtatyg gtt 23

<210> SEQ ID NO 5
<211> LENGTH: 35
<212> TYPE: DNA
<213> ORGANISM: Artificial Sequence
<220> FEATURE:
<223> OTHER INFORMATION: First specific primer

<400> SEQUENCE: 5
ttttaattta gaatttatta ttatttgaag tttta 35

<210> SEQ ID NO 6
<211> LENGTH: 35
<212> TYPE: DNA
<213> ORGANISM: Artificial Sequence
<220> FEATURE:
<223> OTHER INFORMATION: First specific primer

<400> SEQUENCE: 6
atttggatyg tatttttaag atatttaatt attaa 35

<210> SEQ ID NO 7
<211> LENGTH: 26
<212> TYPE: DNA
<213> ORGANISM: Artificial Sequence
<220> FEATURE:
<223> OTHER INFORMATION: First specific primer

<400> SEQUENCE: 7
tgtgtttyta taaaggttag gagttt 26

<210> SEQ ID NO 8
<211> LENGTH: 21
<212> TYPE: DNA
<213> ORGANISM: Artificial Sequence
<220> FEATURE:
<223> OTHER INFORMATION: First specific primer

<400> SEQUENCE: 8
gggtggttga tttatgtayg g 21

<210> SEQ ID NO 9
<211> LENGTH: 23
<212> TYPE: DNA
<213> ORGANISM: Artificial Sequence
<220> FEATURE:
<223> OTHER INFORMATION: First specific primer

<400> SEQUENCE: 9
agattgtgyg gtagtaagtt ttt 23

<210> SEQ ID NO 10

<211> LENGTH: 17
<212> TYPE: DNA
<213> ORGANISM: Artificial Sequence
<220> FEATURE:
<223> OTHER INFORMATION: First specific primer

<400> SEQUENCE: 10
gtttgtttgy gygtttg 17

<210> SEQ ID NO 11
<211> LENGTH: 38
<212> TYPE: DNA
<213> ORGANISM: Artificial Sequence
<220> FEATURE:
<223> OTHER INFORMATION: Second specific primer

<400> SEQUENCE: 11
acatggctac gatccgactt ggagtttygg ggygygtg 38

<210> SEQ ID NO 12
<211> LENGTH: 50
<212> TYPE: DNA
<213> ORGANISM: Artificial Sequence
<220> FEATURE:
<223> OTHER INFORMATION: Second specific primer

<400> SEQUENCE: 12
acatggctac gatccgactt tttttgatat tgaaaatgta attggttttt 50

<210> SEQ ID NO 13
<211> LENGTH: 38
<212> TYPE: DNA
<213> ORGANISM: Artificial Sequence
<220> FEATURE:
<223> OTHER INFORMATION: Second specific primer

<400> SEQUENCE: 13
acatggctac gatccgactt ggtytyggtt ggygtttt 38

<210> SEQ ID NO 14
<211> LENGTH: 55
<212> TYPE: DNA
<213> ORGANISM: Artificial Sequence
<220> FEATURE:
<223> OTHER INFORMATION: Second specific primer

<400> SEQUENCE: 14
acatggctac gatccgactt ggagtatttt atttttgttg tttattatta ttttt 55

<210> SEQ ID NO 15
<211> LENGTH: 50
<212> TYPE: DNA
<213> ORGANISM: Artificial Sequence
<220> FEATURE:
<223> OTHER INFORMATION: Second specific primer

<400> SEQUENCE: 15
acatggctac gatccgactt gttgaagtga gaatgtgatt attaattttt 50

<210> SEQ ID NO 16
<211> LENGTH: 54
<212> TYPE: DNA
<213> ORGANISM: Artificial Sequence
<220> FEATURE:
<223> OTHER INFORMATION: Second specific primer

<400> SEQUENCE: 16
acatggctac gatccgactt gtgtgtgtgt gtgtatttat atatttatat aaaa 54

<210> SEQ ID NO 17
<211> LENGTH: 50
<212> TYPE: DNA
<213> ORGANISM: Artificial Sequence
<220> FEATURE:
<223> OTHER INFORMATION: Second specific primer

<400> SEQUENCE: 17
acatggctac gatccgactt ttagaattga gattagagag gtaagtaatg 50

<210> SEQ ID NO 18
<211> LENGTH: 48
<212> TYPE: DNA
<213> ORGANISM: Artificial Sequence
<220> FEATURE:
<223> OTHER INFORMATION: Second specific primer

<400> SEQUENCE: 18
acatggctac gatccgactt gttaagttga aaagttgaat ttgttttt 48

<210> SEQ ID NO 19
<211> LENGTH: 45
<212> TYPE: DNA
<213> ORGANISM: Artificial Sequence
<220> FEATURE:
<223> OTHER INFORMATION: Second specific primer

<400> SEQUENCE: 19
acatggctac gatccgactt ygggttgttt ttgtatttat tgttg 45

<210> SEQ ID NO 20
<211> LENGTH: 43
<212> TYPE: DNA
<213> ORGANISM: Artificial Sequence
<220> FEATURE:
<223> OTHER INFORMATION: Second specific primer

<400> SEQUENCE: 20
acatggctac gatccgactt gtatttyggt aatttygagg ttg 43

<210> SEQ ID NO 21
<211> LENGTH: 17
<212> TYPE: DNA
<213> ORGANISM: Artificial Sequence
<220> FEATURE:
<223> OTHER INFORMATION: First universal primer

<400> SEQUENCE: 21
cgcttggcct ccgactt 17

<210> SEQ ID NO 22
<211> LENGTH: 25
<212> TYPE: DNA
<213> ORGANISM: Artificial Sequence
<220> FEATURE:
<223> OTHER INFORMATION: Second universal primer
<220> FEATURE:
<221> NAME/KEY: misc_feature
<222> LOCATION: (1)..(1)
<223> OTHER INFORMATION: Phosphorylation

<400> SEQUENCE: 22
gaacgacatg gctacgatcc gactt 25

<210> SEQ ID NO 23
<211> LENGTH: 58
<212> TYPE: DNA
<213> ORGANISM: Artificial Sequence
<220> FEATURE:
<223> OTHER INFORMATION: Tag primer
<220> FEATURE:
<221> NAME/KEY: misc_feature
<222> LOCATION: (17)..(26)
<223> OTHER INFORMATION: n is a, c, g, or t

<400> SEQUENCE: 23
tgtgagccaa ggagttnnnn nnnnnnttgt cttcctaaga ccgcttggcc tccgactt 58

<210> SEQ ID NO 24
<211> LENGTH: 25
<212> TYPE: DNA
<213> ORGANISM: Artificial Sequence
<220> FEATURE:
<223> OTHER INFORMATION: First sequencing primer
<220> FEATURE:
<221> NAME/KEY: misc_feature
<222> LOCATION: (18)..(25)
<223> OTHER INFORMATION: n is a, c, g, or t

<400> SEQUENCE: 24
cgcttggcct ccgacttnnn nnnnn 25

<210> SEQ ID NO 25
<211> LENGTH: 18
<212> TYPE: DNA
<213> ORGANISM: Artificial Sequence
<220> FEATURE:
<223> OTHER INFORMATION: Adapter 1
<220> FEATURE:
<221> NAME/KEY: misc_feature
<222> LOCATION: (1)..(1)
<223> OTHER INFORMATION: Phosphorylation
<220> FEATURE:
<221> NAME/KEY: misc_feature
<222> LOCATION: (1)..(18)
<223> OTHER INFORMATION: A base C is methylated.
<220> FEATURE:
<221> NAME/KEY: misc_feature
<222> LOCATION: (1)..(18)
<223> OTHER INFORMATION: Any base C is methylated.

<400> SEQUENCE: 25
agtcggaggc caagcggt 18

<210> SEQ ID NO 26
<211> LENGTH: 20
<212> TYPE: DNA
<213> ORGANISM: Artificial Sequence
<220> FEATURE:
<223> OTHER INFORMATION: Adapter 2
<220> FEATURE:
<221> NAME/KEY: misc_feature
<222> LOCATION: (20)..(20)
<223> OTHER INFORMATION: Dideoxy

<400> SEQUENCE: 26
acatggctac gatccgactt 20

METHOD AND SYSTEM FOR CONSTRUCTING SEQUENCING LIBRARY ON THE BASIS OF METHYLATED DNA TARGET REGION, AND USE THEREOF

CROSS-REFERENCE TO RELATED APPLICATIONS

This application is a continuation of International Application No. PCT/CN2019/087824, filed on May 21, 2019, which is incorporated herein by reference in its entirety.

STATEMENT REGARDING SEQUENCE LISTING

A Sequence Listing associated with this application is being filed concurrently herewith in ASCII format and is hereby incorporated by reference into the present specification. The text file containing the Sequence listing is titled "Sequence_Listing.txt", was created on Oct. 5, 2021, and is 5,811 bytes in size.

FIELD

The present disclosure relates to the field of gene sequencing, and in particular to a method and system for constructing a sequencing library based on a target region of methylated DNA, and use thereof.

BACKGROUND

DNA methylation is an epigenetic regulatory modification, which participates in the regulation of the quantity of synthetized proteins without changing the base sequence. For humans, DNA methylation is a very amazing chemical modification, which truthfully records care from relatives, body aging, smoking, alcoholism or even obesity on a genome. The genome is like a diary, and the methylation is the text recording the experience of the human body. DNA methylation is important epigenetic marker information, and it is of great significance for the study of epigenetic space-time specificity to obtain the methylation level data of all C sites in the whole genome. Based on the new generation high-throughput sequencing platform, mapping the DNA methylation level of the whole genome and analyzing the high-precision methylation modification patterns of specific species will surely have a milestone significance in epigenomics research, and lay a foundation for basic mechanism research such as cell differentiation and tissue development, as well as animal and plant breeding, human health and disease research.

Whole Genome Bisulfite Sequencing (WGBS) is the most common method to study biological methylation, which can cover all methylation sites and obtain a more comprehensive methylation profile. However, it has encountered many challenges in the high-throughput sequencing: 1. bisulfite treatment will single-strand DNA and cause serious damage; 2. unmethylated C bases will be converted into U bases after bisulfite treatment, and the GC content of the entire genome will change extremely, resulting in great preference for subsequent amplification; 3. library construction requires microgram-level starting DNAs, but it is difficult to have a very effective method for constructing a library from trace DNAs. For clinical testing and certain specific studies, the operations of the whole-genome methylation sequencing are complicated and the cost thereof is too expensive, while the use of methylation-targeted sequencing technology can effectively solve these problems.

The methylation-targeted sequencing technology can be divided into probe capture-based sequencing technology and multiplex-PCR-based sequencing technology. Probe capture requires a high starting amount, and thus it is difficult to capture some trace samples such as plasma free DNA. Moreover, the design and operation process of a probe of the probe capture are too complicated, the detection period is long, and the cost is high. The multiplex-PCR based on bisulfite-treated DNAs requires a low starting amount, with simple operation and high sensitivity, but this technology needs further improvement.

SUMMARY

The present disclosure aims to solve one of the technical problems in the related art at least to a certain extent. To this end, an object of the present disclosure is to provide a method and a system for constructing a sequencing library based on a target region of methylated DNA and applications thereof. The method provided by the present disclosure performs library-constructing on the target region of the methylated DNA sample, and during the library-constructing, only one strand of the methylated DNA sample is amplified to construct the library. The target product can be obtained by designing specific primers and universal primers for amplification, which can effectively solve the problem of primer dimers. Meanwhile, the specificity of amplification can be guaranteed by using multiple specific primers to amplify the same target region of the methylated DNA template.

Applicant of the present disclosure noticed in the research process that multiplex-PCR based on bisulfite-treated DNA is simple in operation and has high sensitivity, but sets high technical requirements. It has been previously reported that single-molecular BS-PCR using microdrop technique can detect about nine thousand targets at the same time, but the starting amount is relatively high, requiring 2 μg of DNAs. In 2015, Lu Wen and other researchers ingeniously developed MCTA-seq based on PCR technology by utilizing the characteristic sequence of CpG island as primer-binding site, which can simultaneously detect the methylation signals of a large number of CpG island regions. This technique is extremely sensitive, and can detect 7.5 pg of gDNA. However, MCTA-seq is more like a fixed CGI Panel and thus it has insufficient flexibility as a targeted sequencing platform. Therefore, it is the future trend to develop a methylation-targeted technique requiring low starting amount and having strong flexibility.

Applicant found through research that it is the specificity of amplification to effectively perform super-multiplex target amplification, and the sequencing of tens of thousands of genomic amplicons is a very challenging task, not to mention the multiplex methylation PCR on the bisulfite-transformed sequences, mainly due to the formation of serious primer dimers during the PCR process. In the process of multiplex-PCR on the bisulfite-treated DNA, the unmethylated cytosine is converted to uracil after the DNA is bisulfite-treated. Since most of the cytosines in the genome is unmethylated, the bases of the most of sequence are transformed from the previous four components of A/T/C/G to components of A/T/G. In conventional PCR, one primer is designed for the positive strand, and one is designed for the complementary strand. Thus, one strand for PCR is an ATG-rich sequence, and the other strand is an ATC-rich sequence; and this "naturally complementary" primer sequences can easily form primer dimers. When the number of primer pairs increases, the formation of primer dimers also increases sharply. In the process of multiplex-PCR, the primers may be exhausted due to the formation of primer dimers, causing the failure of multiplex-PCR. Therefore, in order to solve the problems in the multiplex-PCR caused by bisulfite, it is necessary to first solve the problem that primers are prone to form primer dimers.

With respect to the problem of primer dimers, we creatively invented a single direction primer amplification method, in which specific primers are designed for only one of the two strands of DNA template, and most of the base in all the specific primers are ATG. These primers can hardly form primer dimers with each other. The target product is obtained through amplification with these one-way specific primers and some universal primers, thereby effectively solving the problem of primer dimers.

Specifically, the present disclosure provides the following technical solutions.

According to the first aspect of the present disclosure, the present disclosure provides a method for constructing a sequencing library based on a target region of a methylated DNA. The method includes: (1) obtaining a transformed DNA sample with universal sequence based on a methylated DNA sample by ligating a universal sequence to at least one end of the methylated DNA sample and treating the methylated DNA sample with bisulfite; (2) performing, by using a first specific primer and a first universal primer, a first amplification on the transformed DNA sample with universal sequence to obtain a first amplification product, wherein the first specific primer is located upstream of the target region, and the first universal primer at least partially matches or overlaps the universal sequence, and the universal primer is located downstream of the target region; and (3) performing, by using a second specific primer, a second universal primer and a tagged primer, a second amplification on the first amplification product to obtain a second amplification product and obtain a sequencing library, wherein the second specific primer is located downstream of the first specific primer and upstream of the target region, the second universal primer overlaps at least a partial sequence of the second specific primer, the tagged primer contains a tag sequence, and the tagged primer overlaps a partial sequence of the first universal primer; or wherein the second specific primer is located downstream of the target region, the second universal primer overlaps at least a partial sequence of the first specific primer, the tagged primer contains a tag sequence, and the tagged primer overlaps a partial sequence of the second specific primer.

The method for constructing a sequencing library based on a target region of a methylated DNA provided by the present disclosure is to design specific primers for one strand of a methylated DNA template for enriching the target regions and constructing a library. First, a universal sequence is introduced to at least one end of the methylated DNA template, and then a bisulfite treatment is performed; or the bisulfite treatment is first performed, and then the universal sequence is introduced. That is, the transformed DNA sample with universal sequence is first obtained. Then, the primers for only one strand of the DNA sample are designed. That is, the first specific primer and the first universal primer are used to amplify one strand of the DNA sample, the first specific primer can match one strand of the DNA sample, and the first universal primer can match the universal sequence, thereby achieving a specific amplification. In addition, since the DNA template used is a bisulfite-transformed sample, the first specific primer is designed to be a sequence rich in bases A, T, and G or rich in bases A, T, and C, and thus they will not form dimers with each other. The first universal primer contains four bases, A, T, C, and G, and will not form primer dimers with the first specific primer. In this way, the formation of primer dimers can be completely avoided.

Meanwhile, in order to ensure the specificity of primer amplification, a second specific primer is designed to be located downstream of the first specific primer and upstream of the target region, or to be located downstream of the target region. The second specific primer, a second universal primer and a tagged primer are used to perform a second amplification on the first amplification product to obtain a second amplification product and obtain the desired sequencing library.

According to an embodiment of the present disclosure, the above-mentioned method for constructing the sequencing library based on the target region of the methylated DNA may further include the following technical features.

In some embodiments of the present disclosure, in the step (3), a 5'-end of the second specific primer overlaps at least a partial sequence of a 3'-end of the second universal primer, and a 3'-end of the tagged primer overlaps a partial sequence of a 5'-end of the first universal primer. The sequence of the 5'-end of the second specific primer can overlap at least a partial sequence of the 3'-end of the second universal primer, and a sequence of a 3'-end of the second specific primer can match a template region on the DNA template downstream of the first specific primer and upstream of the target region. Therefore, the target region can be specifically amplified based on the first amplification product.

In some embodiments of the present disclosure, in the step (3), a 5'-end of the second specific primer overlaps at least a partial sequence of a 3'-end of the tagged primer, and a 3'-end of the second universal primer overlaps a partial sequence of a 5'-end of the first specific primer. A sequence of the 5'-end of the second specific primer overlaps at least a partial sequence of the 3'-end of the tagged primer, and a sequence of a 3'-end of the second specific primer can match a template region on the DNA template downstream of the target region, thereby achieving the specific amplification of the target region.

In some embodiments of the present disclosure, the tagged primer contains a tag sequence. The tag sequence can be tag sequences commonly used by some sequencing platforms to distinguish different samples, for facilitating simultaneously sequencing of multiple mixed samples. According to an embodiment, a length of these tag sequences can be 8 bp to 12 bp, for example, 10 bp, 8 bp, etc.

In some embodiments of the present disclosure, the step (1) further includes: (1-a) treating the methylated DNA sample with bisulfite to obtain a transformed DNA sample; and (1-b) replicating the transformed DNA sample by using a DNA polymerase and a random primer having a first sequencing sequence to obtain the transformed DNA sample with universal sequence. A 3'-end of the random primer is a sequence of random bases, and a 5'-end of the random primer is the universal sequence.

In some embodiments of the present disclosure, the sequence of random bases includes 6 to 12 random bases, and the random bases are A, T, C, or G.

In some embodiments of the present disclosure, the sequence of random bases includes 6 to 12 random bases, and the random bases are A, T or C.

In some embodiments of the present disclosure, the universal sequence is a sequencing adapter sequence or a known sequence.

In some embodiments of the present disclosure, cytosine in the sequencing adapter sequence or the known sequence is methylated cytosine.

In some embodiments of the present disclosure, the step (1) further includes: (1-1) performing end repair by adding A-tailing to the methylated DNA sample to obtain a repaired DNA sample; (1-2) ligating the universal sequence to at least one end of the repaired DNA sample to obtain a DNA sample with universal sequence; and (1-3) treating the DNA sample with universal sequence by using bisulfite to obtain the transformed DNA sample with universal sequence.

In some embodiments of the present disclosure, the universal sequence is at least one selected from a sequencing adaptor sequence or a modified sequencing adaptor sequence.

In some embodiments of the present disclosure, the modified sequencing adapter sequence is a sequencing adapter sequence in which cytosines on one strand are methylated and cytosines on the other strand are unmethylated; a sequencing adapter sequence with a known sequence and a random sequence, a base at a 3'-end of one strand of the sequencing adapter being not modified with a non-hydroxy group; or a sequencing adapter sequence with a known sequence and a random sequence, a base at a 3'-end of one strand of the sequencing adapter being modified by a non-hydroxy group.

In some embodiments of the present disclosure, the random sequence is a molecular tag sequence. The number of original DNA templates can be counted through a large number of different molecular tag sequences, and through subsequent statistics of the molecular tag sequences, the number of original templates can be traced and errors generated in the sequencing or PCR process can be corrected, thereby achieving the precise detection and quantitative research of DNA templates.

In some embodiments of the present disclosure, the step (1) further includes: ① interrupting and transposing the DNA sample by using a transposase to obtain a DNA sample with universal sequence, wherein the transposase is embedded with the universal sequence; and ② treating the DNA sample with universal sequence by using bisulfite to obtain the transformed DNA sample with universal sequence.

In some embodiments of the present disclosure, the universal sequence is a transposase effector sequence or a transposase effector sequence with sequencing adapter, preferably the transposase effector sequence. The transposase can be Tn5, MuA or other transposases with similar functions, preferably Tn5 transposase.

In some embodiments of the present disclosure, cytosine in the transposase effector sequence is methylated cytosine. Not 100% of the unmethylated cytosines are converted to guanine, i.e., the unmethylated cytosines may or may not be converted, which increases the uncertainty in the subsequent amplification with universal primers. The methylated cytosine will not be converted to uracil under the condition of subsequent sulfite treatment, and maintains the sequence information unchanged. Therefore, for the more accurate sequencing, the cytosines in the transposase effector sequence can be modified through methylation. Of course, it is also possible that cytosines are not modified through methylation treatment.

In some embodiments of the present disclosure, the methylated DNA sample is genomic DNA, fragmented genomic DNA, or free DNA.

According to the second aspect of the present disclosure, the present disclosure provides a system for constructing a sequencing library based on a target region of methylated DNA. The system includes: a universal transformation module configured to obtain a transformed DNA sample with universal sequence based on a methylated DNA sample by ligating a universal sequence to at least one end of the methylated DNA sample and treating the methylated DNA sample with bisulfite; a first amplification module connected to the universal transformation module, the first amplification module being configured to perform, by using a first specific primer and a first universal primer, a first amplification on the transformed DNA sample with universal sequence to obtain a first amplification product, wherein the first specific primer is located upstream of the target region, and the first universal primer at least partially matches or overlaps the universal sequence; and a second amplification module connected to the first amplification module, the second amplification module being configured to perform, by using a second specific primer, a second universal primer and a tagged primer, a second amplification on the first amplification product to obtain a second amplification product and obtain the sequencing library, wherein second specific primer is located downstream of the first specific primer and upstream of the target region, the second universal primer overlaps at least a partial sequence of the second specific primer, the tagged primer contains a tag sequence, and the tagged primer overlaps a partial sequence of the first universal primer; or, wherein the second specific primer is located downstream of the target region, the second universal primer overlaps at least a partial sequence of the first specific primer, the tagged primer contains a tag sequence, and the tagged primer overlaps a partial sequence of the second specific primer.

According to an embodiment of the present disclosure, the above-mentioned system for constructing the sequencing library based on the target region of methylated DNA may further include the following technical features.

In some embodiments of the present disclosure, in the second amplification module in the above system, a 5'-end of the second specific primer overlaps at least a partial sequence of a 3'-end of the second universal primer, and a 3'-end of the tagged primer overlaps a partial sequence of a 5'-end of the first universal primer.

In some embodiments of the present disclosure, in the second amplification module in the above system, a 5'-end of the second specific primer overlaps at least a partial sequence of a 3'-end of the tagged primer, and a 3'-end of the second universal primer overlaps a partial sequence of a 5'-end of the first specific primer.

In some embodiments of the present disclosure, in the above system, a length of the tag sequence ranges 8 bp to 12 bp.

In some embodiments of the present disclosure, the universal transformation module further includes: a transformation unit configured to treat the methylated DNA sample with bisulfite to obtain a transformed DNA sample; and an amplification unit connected to the transformation unit, wherein the amplification unit is configured to replicate the transformed DNA sample by using a DNA polymerase and a first sequencing primer to obtain the transformed DNA sample with universal sequence, a 3'-end of the first sequencing primer comprises random bases, and a 5'-end of the first sequencing primer is a universal sequence.

In some embodiments of the present disclosure, in the above system, the number of the random bases is 6 to 12, and the random bases are A, T, C, or G.

In some embodiments of the present disclosure, in the above system, the number of the random bases is 6 to 12, and the random bases are A, T or C.

In some embodiments of the present disclosure, in the above system, the universal sequence is a sequencing adapter sequence or a known sequence.

In some embodiments of the present disclosure, in the above system, cytosine in the sequencing adapter sequence or the known sequence is methylated cytosine.

In some embodiments of the present disclosure, the universal transformation module further includes: a repair unit configured to perform end repair by adding A-tailing to the methylated DNA sample to obtain a repaired DNA sample; a ligation unit connected to the repair unit, wherein the ligation unit is configured to ligate the universal sequence to at least one end of the repaired DNA sample to obtain a DNA sample with universal sequence; and a transformation unit connected to the ligation unit, wherein the transformation unit is configured to treat the DNA sample with universal sequence by using bisulfite to obtain the transformed DNA sample with universal sequence.

In some embodiments of the present disclosure, in the universal transformation module, the universal sequence is at least one selected from a sequencing adapter sequence or a modified sequencing adapter sequence.

In some embodiments of the present disclosure, in the universal conversion module, optionally, the modified sequencing adapter sequence is a sequencing adapter sequence in which cytosines on one strand are methylated and cytosines on the other strand are unmethylated; a sequencing adapter sequence with a known sequence and a random sequence, a base at a 3'-end of one strand of the sequencing adapter being not modified with a non-hydroxy group; or a sequencing adapter sequence with a known sequence and a random sequence, a base at a 3'-end of one strand of the sequencing adapter being modified by a non-hydroxy group.

In some embodiments of the present disclosure, in the universal transformation module, the random sequence is a molecular tag sequence. The number of original DNA templates can be counted through a large number of different molecular marker sequences, and through subsequent statistics of molecular tag sequences, the number of original templates can be traced and errors generated during sequencing or PCR can be corrected, thereby achieving the precise detection and quantitative research of DNA templates.

In some embodiments of the present disclosure, the universal transformation module further includes: a transposition unit configured to interrupt and transpose the DNA sample by using a transposase to obtain a DNA sample with universal sequence, wherein the transposase is embedded with the universal sequence; and a transformation unit connected to the transposition unit, wherein the transformation unit is configured to treat the DNA sample with universal sequence by using bisulfite to obtain the transformed DNA sample with universal sequence.

In some embodiments of the present disclosure, in the above transposable unit, the universal sequence is a transposase effector sequence or a transposase effector sequence with sequencing adapter, preferably the transposase effector sequence.

In some embodiments of the present disclosure, in the above transposable unit, cytosine in the transposase effector sequence is methylated cytosine.

In some embodiments of the present disclosure, the methylated DNA sample is genomic DNA, fragmented genomic DNA, or free DNA.

The foregoing description with respect to the advantages and technical features of the method for constructing the sequencing library based on the target region of methylated DNA in any embodiment of the present disclosure is also applicable to the system for constructing the sequencing library based on the target region of methylated DNA in any of the above embodiments of the present disclosure, which will not be repeated herein.

According to a third aspect of the present disclosure, the present disclosure provides a method for sequencing a methylated DNA sample. The method includes: constructing and obtaining a sequencing library based on the methylated DNA sample by the method described in any embodiments according to the first aspect of the present disclosure or the system described in any embodiments according to the second aspect of the present disclosure; and performing a high-throughput sequencing on the sequencing library to obtain sequencing results.

In some embodiments of the present disclosure, the high-throughput sequencing is performed on the sequencing library by using a sequencing platform, and the sequencing platform is at least one selected from MGISEQ, Illumina, or Proton.

According to a fourth aspect of the present disclosure, the present disclosure provides a method for determining a methylation status of a methylated DNA sample. The method includes: constructing and obtaining a sequencing library based on the methylated DNA sample by the method described in any embodiments according to the first aspect of the present disclosure or the system described in any embodiments according to the second aspect of the present disclosure; performing a high-throughput sequencing on the sequencing library to obtain sequencing results; and aligning the sequencing results to a reference genome to determine the methylation status of the methylated DNA sample.

In some embodiments of the present disclosure, the reference genome is a human genome hg19 or a Yanhuang genome.

According to a fifth aspect of the present disclosure, the present disclosure provides a kit. The kit includes a universal sequence, a tagged primer, a first universal primer, a second universal primer and a conventional methylation detection reagent. The tagged primer contains a tag sequence, the first universal primer matches or overlaps at least part of the universal sequence, the first universal primer is set forth as SEQ ID NO:1, and the second universal primer is set forth as SEQ ID NO:22. The conventional methylation detection reagent can be, for example, a bisulfite detection reagent or a corresponding kit.

According to an embodiment of the present disclosure, the kit described above further includes the following additional technical features:

In some embodiments of the present disclosure, the tagged primer is set forth as SEQ ID NO:23.

In some embodiments of the present disclosure, the kit further includes: a first specific primer and a second specific primer, the first specific primer includes sequences set forth as SEQ ID NO: 1 to SEQ ID NO: 10, and the second specific primer includes sequences set forth as SEQ ID NO: 11 to SEQ ID NO: 20.

In some embodiments of the present disclosure, the kit is configured to construct a sequencing library based on the target region of the methylated DNA by the method described in the first aspect of the present disclosure.

BRIEF DESCRIPTION OF DRAWINGS

The above and/or additional aspects and advantages of the present disclosure will become apparent and easy to understand in conjunction with the description of the embodiments with reference to the following drawings, in which.

DESCRIPTION OF EMBODIMENTS

Figures 1A, 1B:
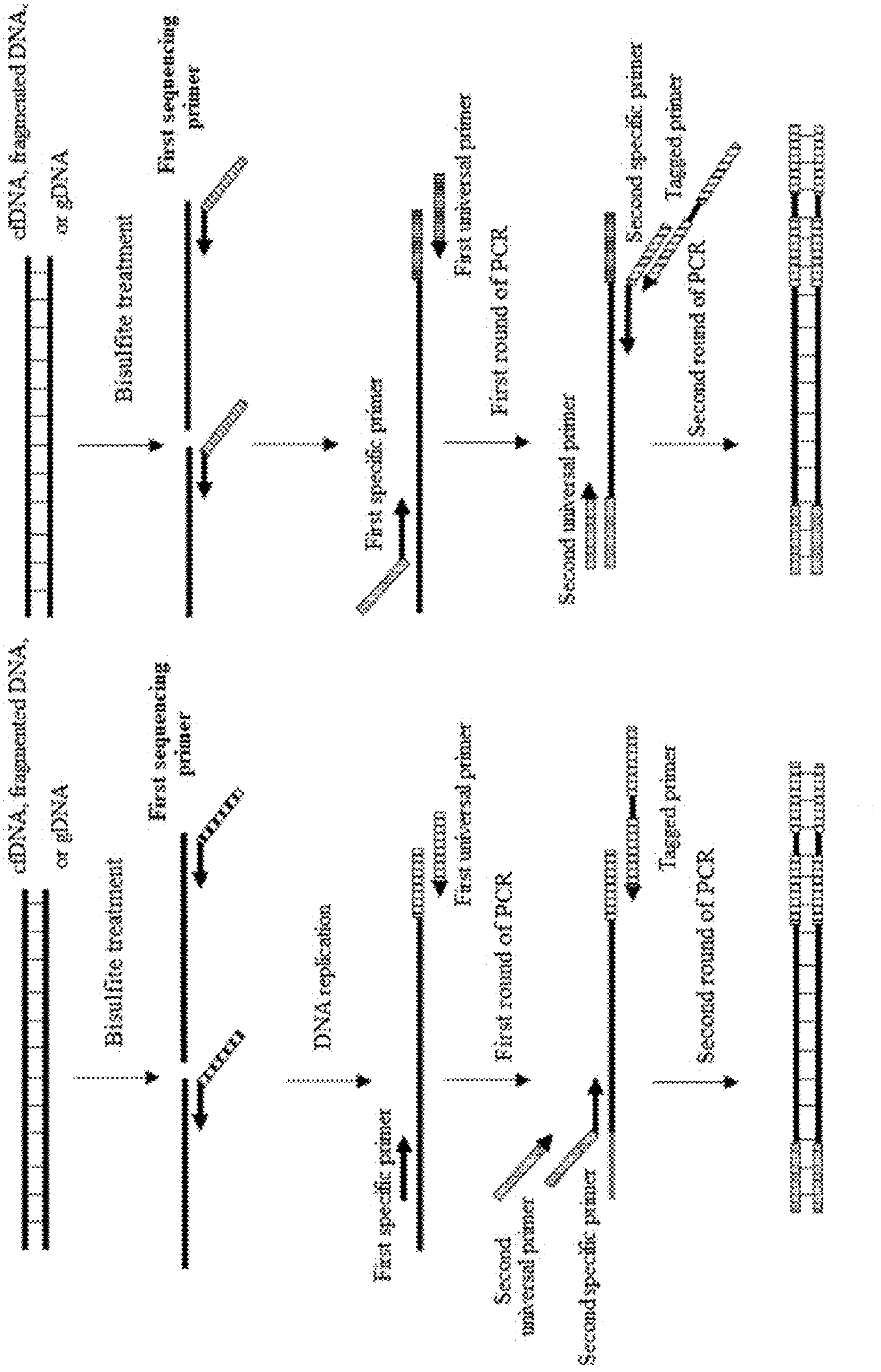
FIG. 1A and FIG. 1B are flow charts of random primer library construction according to an embodiment of the present disclosure.

The embodiments of the present disclosure are described in detail below. Examples of the embodiments are illustrated in the accompanying drawings, throughout which the same or similar reference signs indicate the same or similar elements or elements with the same or similar functions throughout the whole text. The embodiments described below with reference to the accompanying drawings are exemplary, and they are intended to explain the present disclosure, but should not be construed as limitations of the present disclosure.

In order to have a more intuitive understanding of the present disclosure, the terms included in the present disclosure are explained and described below. Those skilled in the art should understand that these explanations and descriptions are only for more convenient understanding, but should not be regarded as limitations of the protection scope of the present disclosure. Herein, unless otherwise specified, where two nucleic acid sequences are described as being connected, it means that they are connected via a 3', 5'-phosphodiester linkage. Unless otherwise specified herein, where a base is mentioned, the base N or n represents any one of bases A, T, C, or G.

Herein, the terms "upstream" and "downstream" refer to that, when comparing two or more nucleic acid sequences according to the order of nucleotides from 5'-end to 3'-end, the nucleic acid sequence located upstream can recognize or match a region closer to the 5'-end of the template sequence than the nucleic acid sequence located downstream. Since different nucleic acid sequences may have different lengths, the regions to be recognized or matched by them may also have different lengths. When it is described that an A nucleic acid sequence is located downstream of a B nucleic acid sequence, it means that a site recognized by or paired with the 3'-end of the A nucleic acid sequence is closer to the 3'-end of the template sequence than a site recognized by or paired with the 3'-end of the B nucleic acid sequence.

Herein, when two nucleic acid sequences are described to "match with each other", it means that bases of one of the two nucleic acid sequences are complementarily paired with bases of the other one nucleic acid sequence. When two nucleic acid sequences are described to be at least partially overlap, it means that the two nucleic acid sequences have at least one fragment of identical nucleic acid sequence.

Herein, either the "bisulfite-" or "sulfite-" treatment refers to a reagent or process that deaminates cytosine in DNA into uracil. Therefore, the bisulfite treatment and the sulfite treatment are included in the protection scope of the present disclosure.

In order to solve the problem of primer dimers between multiple pairs of methylated specific primers in the process of amplifying methylated DNA, the present disclosure creatively provides a one-way primer amplification method, that is, only primers for one strand of the DNA template are designed. In this regard, the designed specific primers each only contain A, T, and G, or A, T, and C, and they can hardly form primer dimers. At the same time, in order to ensure the specificity of primer amplification, during the second round of PCR amplification, specific primers for amplification are designed on the product of the first round of amplification to further ensure the specificity of amplification. The sequencing library prepared in such manner meets the requirements of sequencing.

In detail, the genomic DNA (gDNA) is transposed by a Tn5 transposon, a universal sequence is introduced to the interrupted gDNA or free DNA (cfDNA) molecules (the original DNAs) through adapter connection or random DNA replication; the DNA introduced with the universal sequence is subjected to a bisulfite treatment (BS treatment) to obtain a bisulfite-transformed DNA sequence, in which the unmethylated cytosine (C) of the original DNA is converted to uracil (U). A universal primer is designed based on the introduced universal sequence, a specific primer is designed to be located upstream of the target region of the transformed DNA sequence, and the specific primer is designed for only one strand on the DNA template. PCR amplification is performed by using the universal primer and the specific primer to obtain the PCR product. At the same time, in order to increase the specificity of amplification, a nested primer is designed to be located downstream of the above-mentioned specific primer or the specific primer is designed to be located downstream of the target region, and either the nested primer or the specific primer is designed for only one strand of the DNA template. A second-step amplification is performed on the product of the first-step PCR by using the nested primer or the downstream specific primer and the universal primer, to finally obtain a product of PCR amplification on the bisulfite-treated template (BS-PCR).

In one aspect of the present disclosure, the present disclosure provides a method for constructing a sequencing library based on a target region of a methylated DNA, the method including: (1) obtaining a transformed DNA sample with universal sequence based on a methylated DNA sample by constructing a bisulfite-treated DNA sample with a universal sequence ligated to at least one end of the methylated DNA sample; (2) preforming, by using the first specific primer and the first universal primer, a first amplification on the transformed DNA sample with universal sequence to obtain a first amplification product, wherein the first specific primer is located upstream of the target region, and the first universal primer at least partially overlaps or matches the universal sequence; and the universal sequence is located downstream of the target region; and (3) performing, by using a second specific primer, a second universal primer and a tagged primer, a second amplification on the first amplification product to obtain a second amplification product and obtain a sequencing library, wherein the second specific primer is located downstream of the first specific primer and upstream of the target region, the second universal primer overlaps at least a partial sequence of the second specific primer, the tagged primer contains a tag sequence, and the tagged primer overlaps a partial sequence of the first universal primer; or wherein the second specific primer is located downstream of the target region, the second universal primer overlaps at least a part a partial sequence of the first specific primer, the tagged primer contains a tag sequence, and the tagged primer overlaps a partial sequence of the second specific primer.

In the process of obtaining the transformed DNA sample with universal sequence, different methods can be adopted depending upon the precedence order of the universal sequence treatment and the bisulfite treatment.

In at least some embodiments of the present disclosure, the universal sequence is introduced by the following method:

1. DNA molecules of gDNA, interrupted gDNA or cfDNA are first treated with bisulfite, and then the template is replicated by using a first sequencing primer and DNA polymerase to obtain a bisulfite-treated DNA template with universal sequence (as shown in FIG. 1). The first sequencing primer is a primer that has 6-12 random N bases (degenerate bases composed of A/T/C/G) or 6-12 random H bases (degenerate bases composed of A/T/C) at a 3'-end, and a partial or complete sequencing adapter sequence or a known sequence (in which cytosine is preferably the methylated cytosine) at a 5'-end. The suitable sequencing adapter sequence includes, but are not limited to, the sequencing adapters of MGI platform as well as the sequencing adapter sequences of Illumina and proton platforms. In at least some embodiments, the suitable DNA polymerase can be conventional rTaq, Fusion, or can be Bst or phi29, etc.

Figure 4:
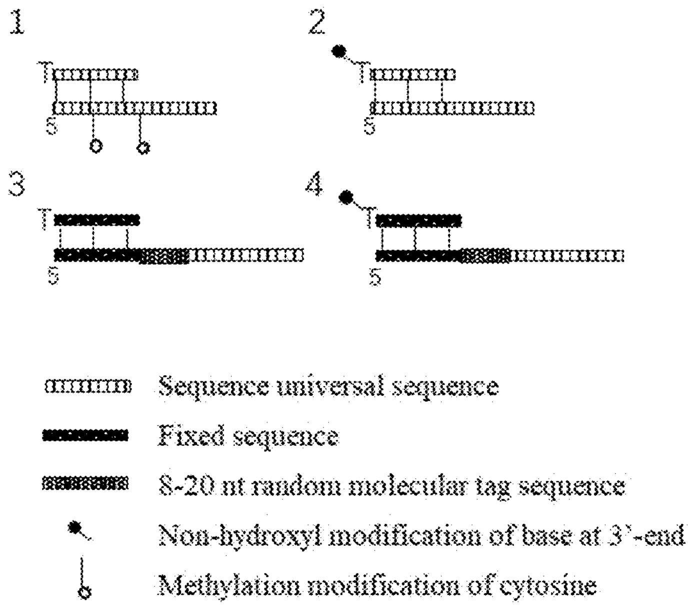
FIG. 4 is a schematic diagram of sequences with different adapters according to an embodiment of the present disclosure.

In at least some embodiments of the present disclosure, the universal sequence is introduced by the following method:

The interrupted gDNA or cfDNA is end-repaired by adding A-tailing, and then a specific adapter sequence is added, which can be partial or complete sequencing adapter sequences or modified sequencing adapter sequences. These modified sequencing adapter sequences each can be a sequencing adapter sequence having a known sequence and one strand with non-hydroxyl modified base at 3'-end, or a sequencing adapter sequence having a known sequence and one strand without non-hydroxyl modified base at 3'-end, for example, No. 1, No. 2, No. 3, and No. 4 shown in FIG. 4. After purification, the product added with the universal sequence is treated with sulfite to obtain the transformed DNA template (FIG. 2).

In some other embodiments of the present disclosure, the universal sequence is introduced by the following method.

Figure 3:
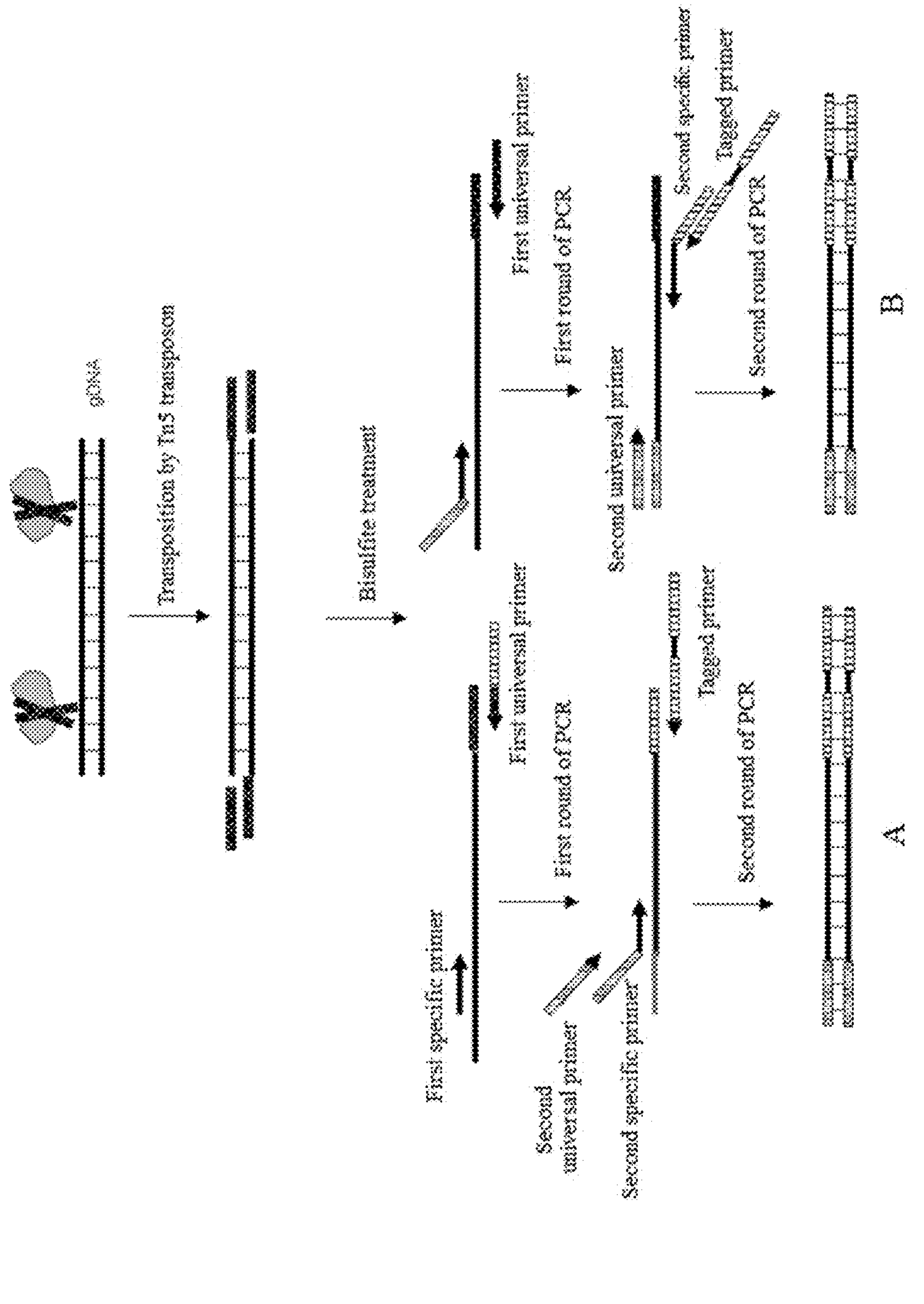
FIG. 3A and FIG. 3B are flow charts of transposon library construction according to an embodiment of the present disclosure.

An adapter sequence is embedded in Tn5 transposase. The adapter can be the effective 19 bp specific sequence of the Tn5 transposase itself, or a combination of the effective sequence and other sequences (such as sequencing adapter sequence), preferably 19 bp specific sequence. The cytosine in the 19 bp specific sequence is preferably methylated cytosine. The gDNA is transposed by Tn5 transposition to be added with a specific adapter. After purification, the product with added the specific adapters is treated with bisulfite to obtain the transformed DNA template (as shown in FIG. 3).

After obtaining the above-mentioned transformed DNA sample with universal sequence, a sequencing library is obtained by PCR amplification is performed with one-way specific primers, and the amplification method can be any one of the followings.

In at least some embodiments of the present disclosure, the sequencing library is obtained by performing PCR amplification by the following method.

Figure 2B:
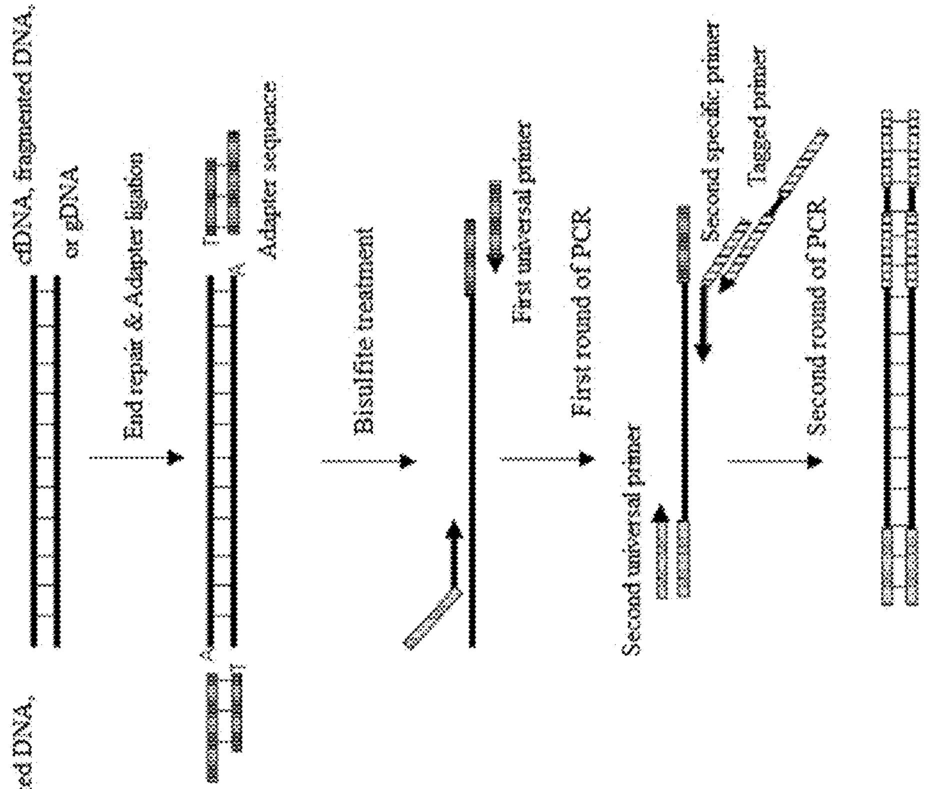
FIG. 2A and FIG. 2B are flow charts of adapter connection library construction according to an embodiment of the present disclosure.
Figure 2A:
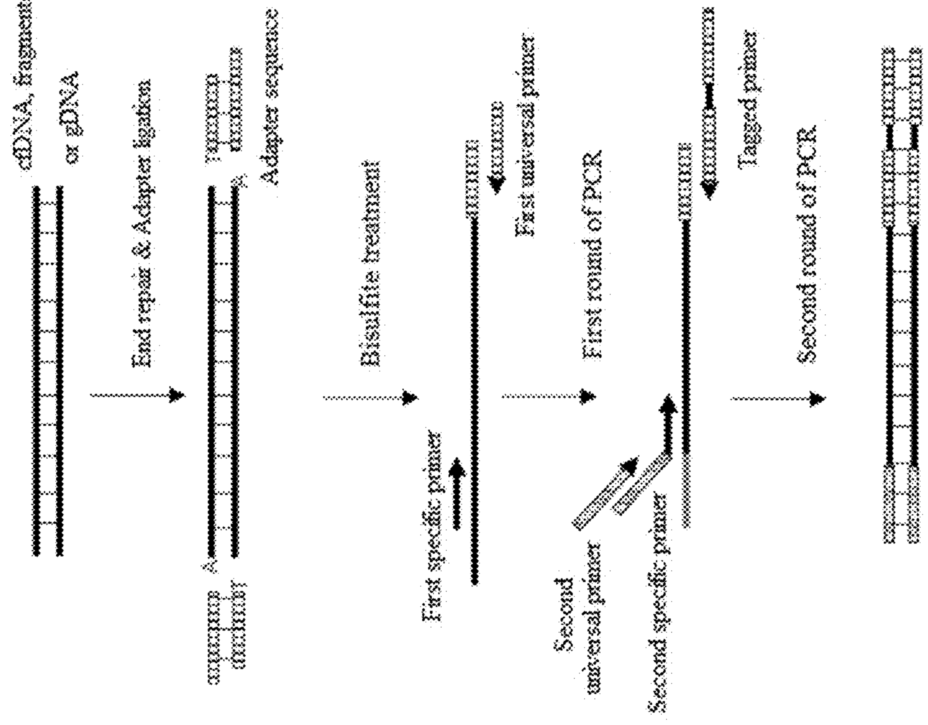

A first-step PCR amplification is performed on the sulfite-treated DNA by using a specific primer and a first universal primer. A sequence of the 3'-end of the first universal primer is partially or completely complementary to or partially or completely overlaps the added universal sequence. For example, the 5'-end of the first universal sequence is a partial or complete sequencing adapter sequence (preferred partial sequence). The binding site of the first specific primer sequence is located upstream of the target region to be amplified, and is designed for the bisulfite-treated DNA template sequence. The obtained product is purified and is then subjected to a second-step PCR amplification by using a second specific primer (also referred to as nested primer in the following examples), a second universal primer, and a tagged primer. In a first cycle of the second-step PCR, the second specific primer and the tagged primer are first subjected to PCR, and the subsequent cycles are performed with the second specific primer, the second universal primer and the tagged primer together, so as to perform multiple rounds of PCR. The 5'-end of the second specific primer overlaps a partial or complete sequence of the 3'-end of the second universal primer. The 3'-end of the second specific primer is a specific sequence, and the specific sequence is designed to be located between the first specific primer and the target region. The second universal primer can be a partial or complete sequence of the sequencing universal adapter, and a 3'-end thereof is identical to a partial or complete sequence of the 5'-end of the second specific primer. The 3'-end of the tagged primer is identical to a partial or complete sequence of the 5'-end of the first universal primer, and a known tag sequence of 8-12 bp is present in the middle of the tagged primer (each platform is used to distinguish the tag sequences of mixed sample), which is used for subsequent multi-sample mixed sequencing (FIG. 1A, FIG. 2A, FIG. 3A).

In some other embodiments of the present disclosure, the sequencing library is obtained by performing PCR amplification by the following method.

A first-step PCR amplification is performed on the sulfite-treated DNA by using a first specific primer (also referred to as the upstream specific primer in the following examples)

and a first universal primer. A sequence of the 3'-end of the first universal primer is partially or completely complementary to or partially or completely overlaps the introduced universal sequence (the universal sequence preferably uses a known sequence other than the sequencing adapter sequence). The specific sequence of the 3'-end of the first specific primer is designed to be located upstream of the target region to be amplified, and is designed specifically for the bisulfite-treated DNA template sequence, and the 5'-end of the first specific primer is a partial or complete sequencing adapter sequence (preferred partial sequence). After the obtained product is purified, a second-step PCR amplification is performed using a second specific primer (referred to as downstream specific primer in the following embodiments, accordingly), a second universal primer, and a tagged primer. In a first cycle of the second-step PCR, the second specific primer and the second universal primer are first subjected to PCR amplification, and in the subsequent cycles, the second specific primer, the second universal primer and the tagged primer together are subjected to multiple rounds of PCR. The 5'-end of the downstream specific primer overlaps a partial or complete sequence of the 3'-end of the tagged primer, and the 3'-end of the second specific primer is a specific sequence. The specific sequence is designed to be located downstream of the target region. The second universal primer can be a partial or complete sequencing adapter sequence, which has a 3'-end overlapping a partial or complete sequence of the 5'-end of the first specific primer. The 3'-end of the tagged primer is identical to a partial or complete sequence of the 5'-end of the second specific primer, and the tagged primer has a known tag sequence of 8-12 bp in the middle (each platform is used to distinguish tag sequences of a mixed sample), which is used for subsequent multi-sample mixed sequencing (FIG. 1B, FIG. 2B, FIG. 3B).

Figure 9:
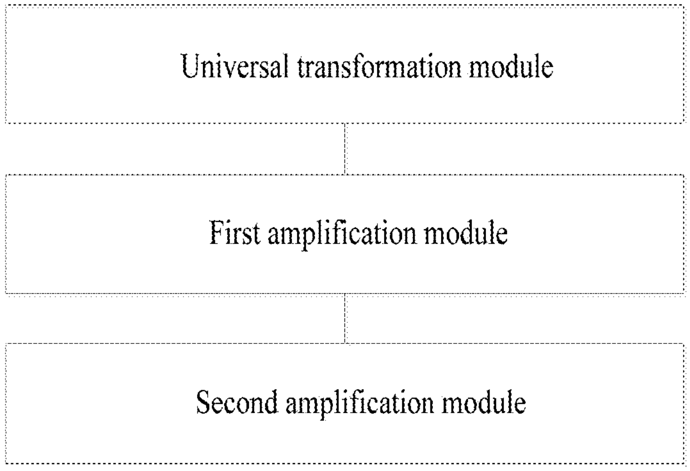
FIG. 9 is a schematic structural diagram of a system for constructing a sequencing library based on a target region of methylated DNA according to an embodiment of the present disclosure.

According to another aspect of the present disclosure, the present disclosure provides a system for constructing a sequencing library based on a target region of a methylated DNA. As illustrated in FIG. 9, the system includes a universal transformation module, a first amplification module, and a second amplification module that are connected in sequence. The universal transformation module is configured to obtain a transformed DNA sample with universal sequence based on a methylated DNA sample by constructing a DNA sample with universal sequence ligated to at least one end thereof and treated with bisulfite. The first amplification module is configured to perform the first amplification on the transformed DNA sample with universal sequence by using the first specific primer and the first universal primer, to obtain a first amplification product. The first specific primer is located upstream of the target region, and the first universal primer at least partially matches or overlaps the universal sequence. The second amplification module is configured to perform a second amplification on the first amplification product by using a second specific primer, a second universal primer, and a tagged primer to obtain a second amplification product and obtain a sequencing library. The second specific primer, the universal primer and the tagged primer are as set forth in (i) or (ii): (i) the second specific primer is located downstream of the first specific primer and upstream of the target region, the second universal primer overlaps at least a partial sequence of the second specific primer, the tagged primer contains a tag sequence, and the tagged primer overlaps a partial sequence of the first universal primer; or (ii) the second specific primer is located downstream of the target region, the second universal primer overlaps at least a partial sequence of the first specific primer, the tagged primer contains a tag sequence, and the tagged primer overlaps a partial sequence of the second specific primer.

Figure 10:
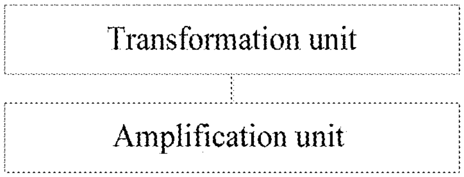
FIG. 10 is a schematic structural diagram of a universal transformation module according to an embodiment of the present disclosure.

In at least some embodiments of the present disclosure, the universal transformation module, as shown in FIG. 10, includes a transformation unit and an amplification unit connected to the transformation unit. The transformation unit is configured to treat the methylated DNA sample with bisulfite to obtain a transformed DNA sample. The amplification unit is configured to replicate the transformed DNA sample by using a DNA polymerase and a first sequencing primer, to obtain the transformed DNA sample with universal sequence. The 3'-end of the first sequencing primer is random bases, and the 5'-end of the first sequencing primer is a universal sequence.

Figure 11:
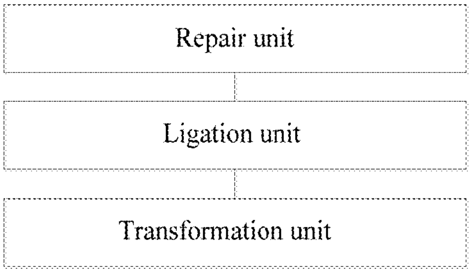
FIG. 11 is a schematic structural diagram of a universal transformation module according to an embodiment of the present disclosure.

In at least some embodiments of the present disclosure, the universal transformation module, as shown in FIG. 11, includes a repair unit, a connection unit, and a transformation unit that are connected in sequence. The repair unit is configured to perform end repair by adding A-tailing on the methylated DNA sample, to obtain a repaired DNA sample. The connecting unit is configured to ligate the universal sequence to at least one end of the repaired DNA sample, to obtain a DNA sample with universal sequence. The transformation unit is configured to treat the DNA sample with universal sequence by using bisulfite, so as to obtain the transformed DNA sample with universal sequence.

Figure 12:
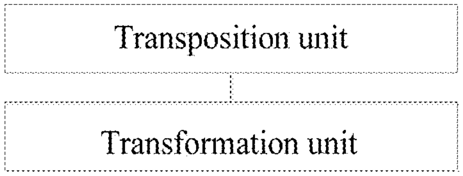
FIG. 12 is a schematic structural diagram of a universal transformation module according to an embodiment of the present disclosure.

In at least some embodiments of the present disclosure, the universal transformation module, as shown in FIG. 12, includes a transposition unit and a transformation unit connected to the transposition unit. The transposable unit is configured to interrupt and transpose the DNA sample by using a transposase (embedded with a universal sequence), to obtain the DNA sample with universal sequence. The transformation unit is configured to treat the DNA sample with universal sequence by using bisulfite, to obtain the transformed DNA sample with universal sequence.

The solutions of the present disclosure will be explained below in conjunction with embodiments. Those skilled in the art can understand that the following embodiments are only used to illustrate the present disclosure, and should not be regarded as limiting the scope of the present disclosure. Wherever specific techniques or conditions are not indicated in the embodiments, the procedures shall be carried out in accordance with the techniques or conditions described in the literatures in the field or in accordance with the product instructions. The reagents or instruments used without indication of the manufacturer are all conventional products that are commercially available.

Example 1: Library Construction and Sequencing Based on Methylation Multiplex-PCR Experimental design: 100 ng of Yanhuang genomic DNAs was subjected to bisulfite treatment, then a DNA target methylation library was prepared by following the steps of the present disclosure, and the library was loaded on MGISEQ-2000™ sequencer for sequencing, with sequencing type PE100, and then the data was analyzed, including data utilization, mappability, amplicon specificity, uniformity, and other properties.

1. Bisulfite Treatment

Using a EZ DNA Methylation-Gold Kit™ (ZYMO™, USA, catalog number D5005), the above-mentioned DNAs were co-treated with bisulfite.

Solution Preparation:

Preparation of CT conversion reagent solution: CT conversion reagent (solid mixture) was taken out from the kit. 900 μL of water, 50 μL of M-dissolving buffer, and 300 μL of M-dissolving buffer were added, respectively. Then, the mixture was dissolved at room temperature and was oscillated for 10 minutes or shaken on a shaker for 10 minutes.

Preparation of M-washing buffer: 24 mL of 100% ethanol was added to the M-Washing Buffer for use.

Specific steps are as follows:

(1) 130 μL of the CT conversion reagent solution and the above DNAs were added to a PCR tube, followed by flicking or pipetting to suspend the mixed sample;

Then, the sample tube was placed on the PCR machine to perform the following steps: 5 minutes at 98° C. and 2.5 hours at 64° C.

After completing the above operations, immediately proceeding to the next step.

(2) the Zymo-Spin IC™ Column was placed into the collection tube, and 600 μL of M-binding buffer was added.

Then, the bisulfite-treated sample was added into the Zymo-Spin IC™ Column containing the M-binding buffer, followed by closing the lid and mixing upside down.

Centrifugation was performed at a full speed (>10,000×g) for 30 seconds, the collection solution in the collection tube was discarded, 100 μL of the M-washing Buffer was added into the column, followed by centrifuging at a full speed (>10,000×g) for 30 seconds and discarding the liquid in the collection tube.

200 μL of M-Desulphonation Buffer was added into the column, stood at room temperature for 15 min, followed by centrifuging at a full speed (>10,000×g) for 30 seconds, and discarding the liquid in the collection tube.

200 μL of the M-wash Buffer was added into the column, followed by centrifuging at a full speed (>10,000×g) for 30 seconds, and discarding the liquid in the collection tube. This step was repeated one more time.

The Zymo-Spin IC™ Column was placed in a new 1.5 mL EP tube, 40 μL of M-elution buffer r was added into the column matrix, and stood at room temperature for 2 min, followed by centrifuging at a full speed (>10,000×g) to elute the target fragment DNA.

2. DNA Replication (1) DNA replication was performed on the bisulfite-treated DNA in the PCR tube according to the following reaction system.

| | |
|---|---|
| Ligated DNA from the previous step | 38 μL |
| 5 × Bst buffer | 5 μL |
| Random primer (10 μM) | 5 μL |
| BST enzyme (NEB, USA, catalog No. M0538) | 1 μL |
| dNTP mix (10 mM) | 1 μL |
| Total volume | 50 μL |

The sequence of the random primer (i.e., the first sequencing primer mentioned in this disclosure): CGCTTGGCCTCCGACTTNNNNNNNN (SEQ ID NO: 24), where N is a random one selected from the group consisting of four bases: A/T/C/G.

(2) The above reaction system was placed on the PCR machine, and reacted at 65° C. for 10 minutes.

(3) After the reaction was complete, purification was performed using 1.5×AMPure magnetic beads (Beckman™, AMPure XP™, catalog No. A63881), and the purified product was finally dissolved in 22 μl of elution buffer. 3. A first round of PCR (1) the PCR System in the PCR Tube was Configured According to the Following Reaction System

| | |
|---|---|
| Treated DNA from the previous step | 20 μL |
| 2 × KAPA2G Fast ReadyMix (Kapa, USA, KK5102) | 25 μL |
| First specific primer pool (10 μM) | 2.5 μL |
| First universal primer (10 μM) | 2.5 μL |
| Total volume | 50 μL |

(2) Reaction Conditions of PCR

94° C. 1 min

94° C. 30 s<br>58° C. 2 min } 15 cycles<br>72° C. 30 s

72° C. 5 min

12° C. maintained (3) Purification was performed with 1.5×AMPure magnetic beads after the reaction was complete, and finally the purified product was dissolved in 22 μl of elution buffer.

3. a Second Round of PCR (1) The PCR system in the PCR tube was configured according to the following reaction system. The nested primer pool is shown in Table 4 below, and the tagged primer is shown in Table 5 below.

| | |
|---|---|
| Treated DNA from the previous step | 17.5 μL |
| 2 × KAPA2G Fast Ready Mix | 25 μL |
| Second specific primer pool (10 μM) | 2.5 μL |
| The second universal primer (10 μM) | 2.5 μL |
| Tagged primer (10 μM) | 2.5 |
| Total volume | 50 μL |

(2) Reaction conditions of PCR

94° C. 1 min

94° C. 30 s<br>58° C. 2 min } 20 cycles<br>72° C. 30 s

72° C. 5 min

12° C. maintained (3) Purification was performed with 1.0×AMPure magnetic beads after the reaction was finished, and finally the purified product was dissolved in 22 μl of elution buffer.

Figure 5:
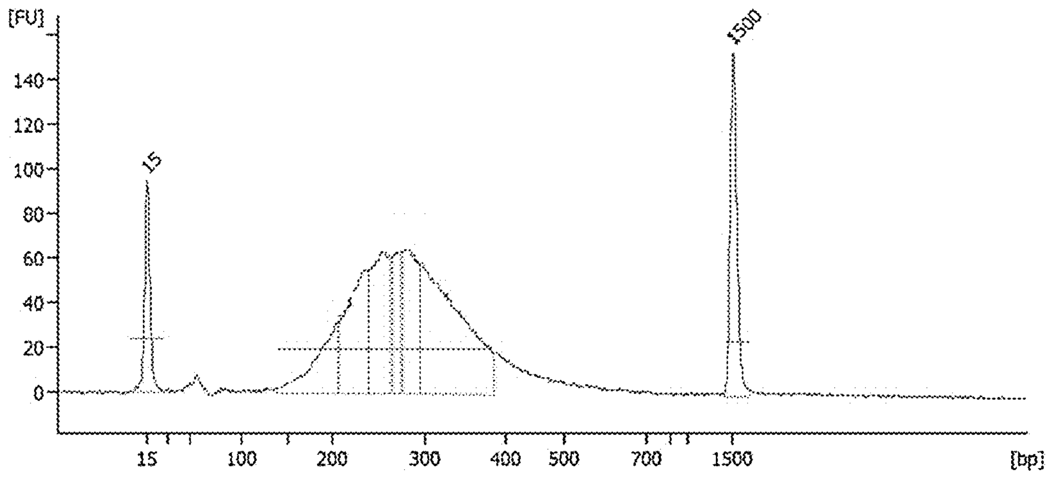
FIG. 5 is a quality inspection graph of a sequencing library according to an embodiment of the present disclosure.

4. Library Detection:

An Bioanalyzer analysis system (Agilent™, Santa Clara, USA) was used to detect the size and content of the inserts in the library, and the results are shown in FIG. 5.

5. On-Machine Sequencing

Figure 6:
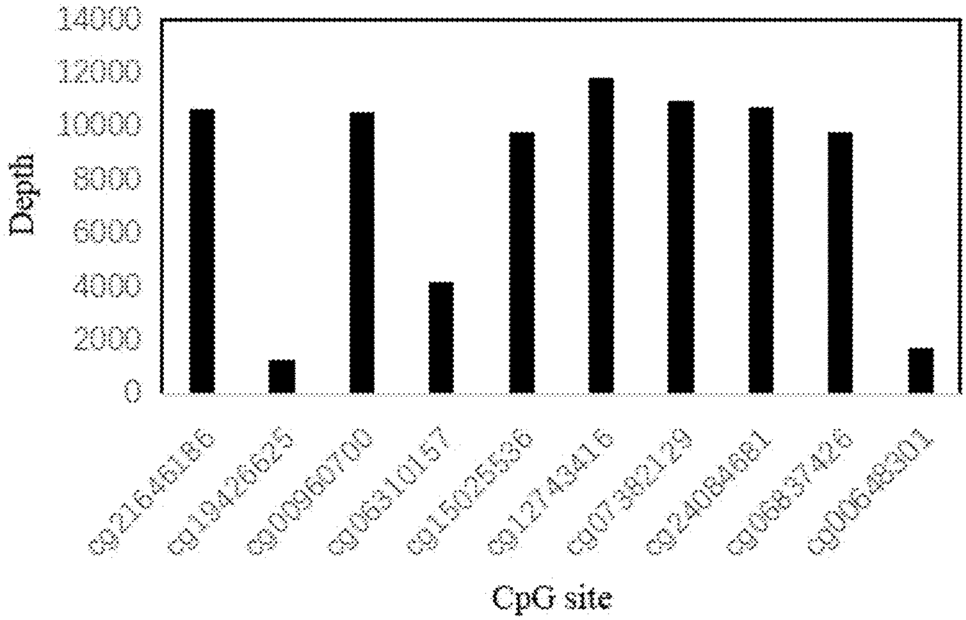
FIG. 6 is a diagram illustrating results of sequencing depths of respective amplicons according to an embodiment of the present disclosure.

High-throughput sequencing was performed on the obtained library with sequencing platform MGISEQ-2000™, sequencing type PE100. After comparing the sequencing data, respective basic parameters, including off-machine data, available data, mappability, GC content, etc. were statistically analyzed. The results are shown in Table 1 below. The depth of each amplicon is shown in FIG. 6. In FIG. 6, the abscissa represents different CpG sites.

Table 1 Sequencing test results

| No. | Off-machine data | Adapter filtration ratio | Mappability | Specificity | 0.1X uniformity |
|---|---|---|---|---|---|
| Sample 1 | 136227 | 1.3% | 89.6% | 78.6% | 90% |
| Sample 2 | 115298 | 1.0% | 88.5% | 77.5% | 90% |
| Sample 3 | 114045 | 0.9% | 88.1% | 78.7% | 90% |

In Table 1, sample 1 to sample 3 represent three replicates of the same sample, respectively; the mappability refers to a mapping ratio with the genome; the specificity refers to a ratio of reads of the target regions to the total reads of the whole sequencing; and the uniformity refers to a proportion of the number of the target regions having a depth 0.1 times greater than an average depth of the target regions to the total number of the target regions.

It can be seen from Table 1 that the adapter filtration ratio of each sample is around 1%, which, in conjunction with the library quality inspection results shown in FIG. 5, indicates an extremely small amount of primer dimers was formed; and the mappabilities are all within a range of 88% to 89%, the specificities are within a range of 77% to 79%, demonstrating good performances. In addition, the depth uniformity of the respective amplicons is good.

Example 2: Library Construction and Sequencing Based on Methylation Multiplex-PCR Experimental design: interrupted Yanhuang genomic DNA of 200-300 bp was used, then a DNA target methylation library was prepared according to the method provided by the present disclosure, and then the library was loaded on a MGISEQ-2000™ sequencer for on-machine sequencing, sequencing type PE100, and then data analysis was performed, including data utilization, mappability, amplicon specificity, uniformity and other properties.

1. End Repair (1) An end repair reaction system was prepared with the DNA fragments obtained in the previous step in a 1.5 mL centrifuge tube according to the following table:

| | |
|---|---|
| DNA fragment | 30 μL |
| $H_2O$ | 45 μL |
| 10 × Polynucleotide kinase buffer (Enzymatic, catalog No. Y9040L) | 10 μL |
| dNTPs (each component was 10 mM) (Enzymatic, catalog No. N2010L) | 4 μL |
| T4 DNA polymerase (Enzymatic, catalog No. P7080L) | 5 μL |
| Klenow fragment (Enzymatic, catalog No. P7060L) | 1 μL |
| T4 polynucleotide kinase (Enzymatic, catalog No. Y9040L) | 5 μL |
| Total volume | 100 μL |

(2) The above reaction system was placed on a Thermomixer (Eppendorf) at 20° C. and reacted for 30 min. After the reaction, purification was performed with AMPure magnetic beads, and finally the purified product was dissolved in 34 μl of elution buffer. The above reagents were all reagents purchased from enzymatic company.

2. Addition of Base A-Tailing (1) A reaction system for adding base A was prepared in a 1.5 mL centrifuge tube from the DNA obtained in the previous step according to the following table.

| | |
|---|---|
| DNA | 32 μL |
| 10 × Klenow buffer (Enzymatic, catalog No. P7010-HC-L) | 5 μL |
| dATP (diluted to 1 mM, Enzymatic, catalog No. N2010-A-L) | 10 μL |
| Klenow (3'-5' exo-, Enzymatic, catalog No. P7010-HC-L) | 3 μL |
| Total volume | 50 μL |

(2) The above reaction system was placed on a Thermomixer (Eppendorf) at 37° C. and reacted for 30 min. After the reaction was complete, purification was performed with AMPure magnetic beads, and the purified product was finally dissolved in 20 μl of elution buffer.

2. Ligation of Methylation Adapter 1:

(1) Methylated adapters (also referred to as "methylated tag adapter") were prepared with the DNA obtained in the previous step according to the following table:

| | |
|---|---|
| DNA | 18 μL |
| 2 × Rapid ligation buffer | 25 μL |
| Methylated tag adapter* | 4 μL |
| T4 DNA ligase (Rapid, enzymatic, L603-HC-L) | 3 μL |
| Total volume | 50 μL |

The sequences of the methylated adapters* are as below:

```
Adapter 1:
                                    (SEQ ID NO: 25)
5'/5Phos/AGTCGGAGGCCAAGCGGT

Adapter 2:
                                    (SEQ ID NO: 26)
5'ACATGGCTACGATCCGACTddT
```

Each cytosine in the sequence of the adapter 1 was methylated for protection, the cytosine in the adapter 2 was methylated for protection or not methylated, and the last base of the 3'-end in the adapter 2 was blocking-modified (i.e., dideoxy-modification) to prevent ligating with the template.

(2) The above reaction system was placed on a Thermomixer (Eppendorf) at 20° C., and reacted for 15 minutes to obtain a ligated product. After the reaction, purification was performed with AMPure magnetic beads, and the purified product was finally dissolved in 22 μl of elution buffer.

3. Sulfite Treatment

Using a kit EZ DNA Methylation-Gold Kit™ (ZYMO™), the above-mentioned ligated DNA was subjected to bisulfite co-treatment.

(1) Reagent Preparation:

Preparation of CT conversion reagent solution: the CT conversion reagent (solid mixture) was taken out from the kit. 900 μL of water, 50 μL of M-dissolving buffer, and 300 μL of M-dissolving buffer were added, respectively. The mixture was dissolved at room temperature and oscillated for 10 minutes or shaken on a shaker for 10 minutes.

Preparation of M-washing buffer: 24 mL of 100% ethanol was added to a M-washing buffer for use.

(2) 130 μL of the CT conversion reagent solution and the above-mentioned ligated DNA to a PCR tube, following by flicking or pipetting to suspend the mixed sample.

Then, the sample tube was placed on a PCR machine to operate according to the steps: 5 minutes at 98° C., and 2.5 hours at 64° C.

After the above operations were finished, immediately proceeding to the next operation or storing the sample at 4° C. (up to 20 hours) for later use.

(3) A Zymo-Spin IC™ Column was placed into a collection tube, and 600 μL of M-binding buffer was added;

Then, the above bisulfite-treated sample was added to the Zymo-Spin IC™ Column containing the M-binding buffer, followed by closing the lid and mixing upside down;

- centrifuging at a full speed (>10,000×g) for 30 seconds and discarding the collection solution in the collection tube;
- adding 100 μL of the M-washing buffer to the column, centrifuging at a full speed (>10,000×g) for 30 seconds, and discarding the liquid in the collection tube;
- adding 200 μL of M-Desulphonation Buffer to the column, leaving it at room temperature for 15 min, centrifuging at a full speed (>10,000×g) for 30 seconds, and discarding the liquid in the collection tube;
- adding 200 μL of the M-washing buffer to the column, centrifuging at a full speed (>10,000×g) for 30 seconds, discarding the liquid in the collection tube, and repeating this step one more time;
- placing the Zymo-Spin IC™ Column in a new 1.5 mL EP tube, adding 18 μL of M-elution buffer r to the column matrix, leaving it at room temperature for 2 min, and centrifuging at a full speed (>10,000×g) to elute the target fragmented DNA.

4. First Round of PCR (1) A PCR system was prepared in a PCR tube according to the following reaction system. The primers contained in the upstream specific primer pool are shown in Table 3 below, and the first universal primer is shown in Table 5 below.

| | |
|---|---|
| Treated DNA from the previous step | 20 μL |
| 2 × KAPA2G Fast Ready Mix | 25 μL |
| First specific primer pool (10 μM) | 2.5 μL |
| First universal primer (10 μM) | 2.5 μL |
| Total volume | 50 μL |

(2) Reaction Conditions for PCR

94° C. 1 min

| | |
|---|---|
| 94° C. 30 s<br>58° C. 2 min<br>72° C. 30 s | 15 cycles |

72° C. 5 min

12° C. maintained

After the reaction was finished, purification was performed with 1.5×AMPure magnetic beads, and finally the purified product was dissolved in 22 μl of elution buffer.

5. Second Round of PCR (1) A PCR system was prepared in the PCR tube according to the following reaction system. The primers contained in the Nested primer pool are shown in Table 4 below, and the second universal primer and the tagged primer are shown in Table 5 below.

| | |
|---|---|
| Treated DNA from the previous step | 17.5 μL |
| 2 × KAPA2G Fast ReadyMix | 25 μL |
| | 2.5 μL |

-continued

| | |
|---|---|
| Second universal primer (10 μM) | 2.5 μL |
| Tagged primer (10 μM) | 2.5 |
| Total volume | 50 μL |

(2) Reaction Conditions for PCR

94° C. 1 min

| | |
|---|---|
| 94° C. 30 s<br>58° C. 2 min<br>72° C. 30 s | 20 cycles |

72° C. 5 min

12° C. maintained

After the reaction was finished, purification was performed with 1.0×AMPure magnetic beads, and finally the purified product was dissolved in 22 μl of elution buffer.

Figure 7:
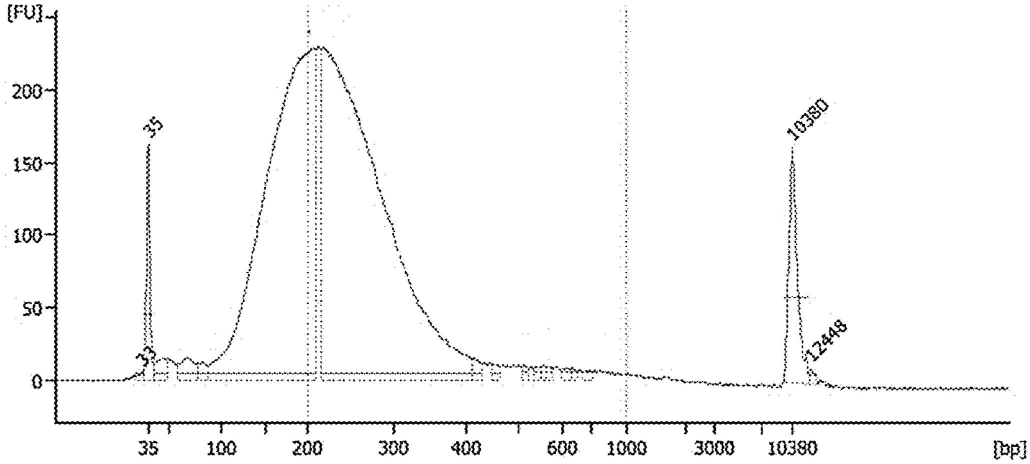
FIG. 7 is a quality inspection graph of a sequencing library according to an embodiment of the present disclosure.

6. Library Detection:

A Bioanalyzer analysis system (Agilent™, Santa Clara, USA) was used to detect the size and content of the inserts in the library, and the results are shown in FIG. 7.

7. On-Machine Sequencing

Figure 8:
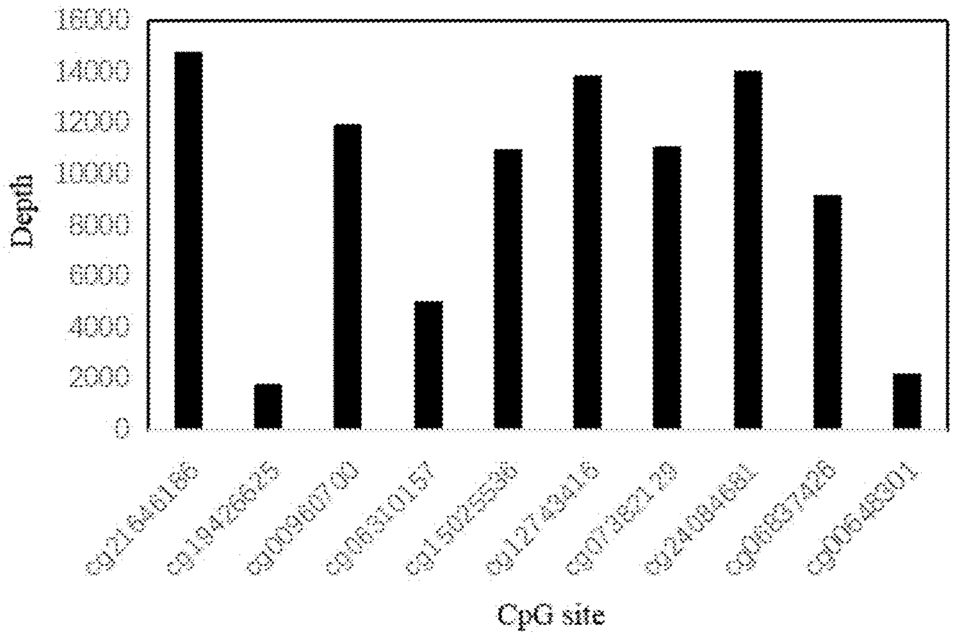
FIG. 8 is a diagram illustrating results of sequencing depths of respective amplicons according to an embodiment of the present disclosure.

High-throughput sequencing was performed on the obtained library using the sequencing platform MGISEQ-2000™ (MGI, sequencing type PE100). After alignment of the sequencing data, the respective basic parameters are statistically analyzed, including off-machine data, available data, mappability, and specificity, etc. The results are shown in Table 2. The sequencing depth of each amplicon is shown in FIG. 8.

TABLE 2

Sequencing results

| No. | Raw data | Adapter filtration rate | Mappability | Specificity | Uniformity |
|---|---|---|---|---|---|
| Sample 1 | 112792 | 0.8% | 84.3% | 89.3% | 100% |
| Sample 2 | 131590 | 1.1% | 85.6% | 90.8% | 100% |
| Sample 3 | 120311 | 0.9% | 86.1% | 90.7% | 100% |

In Table 2, Sample 1 to Sample 3 represent three replicates of one same sample, respectively; the mappability refers to a ratio of mapping to the genome; the specificity refers to a ratio of reads of the target regions to the total reads of the whole sequencing; the uniformity refers to a ratio of the number of target regions having a depth that is 0.1 times greater than an average depth of the target regions to the total number of the target regions.

It can be seen from the results in Table 2, FIG. 7 and FIG. 8 that, using the amplification method provided by the present disclosure, the adapter filtration rate is around 1%, with few primer dimers, and the mappability is in a range of 84% to 86%, the specificity is in a range of 89% to 90%, demonstrating good performances and uniform coverage depth between the amplicons.

TABLE 3

| First specific primer pool | | |
|---|---|---|
| Target CpG sites | No. | Sequence |
| cg21646186 | First specific primer 01 | GGAGGYSTAGYGATTTTAG (SEQ ID NO: 1) |
| cg19426625 | First specific primer 02 | GGGAGAATTTTGAAAATGAAATATATTTTT (SEQ ID NO: 2) |
| cg00960700 | First specific primer 03 | TTTTYGTTTTTYGTTTTYGTTTTT (SEQ ID NO: 3) |
| cg06310157 | First specific primer 04 | TTTTTGAATTYGAGGTATYGGTT (SEQ ID NO: 4) |
| cg15025536 | First specific primer 05 | TTTTAATTTAGAATTTATTATTATTTGAAGTTTTA (SEQ ID NO: 5) |
| cg12743416 | First specific primer 06 | ATTTGGATYGTATTTTTAAGATATTTAATTATTAA (SEQ ID NO: 6) |
| cg07382129 | First specific primer 07 | TGTGTTTYTATAAAGGTTAGGAGTTT (SEQ ID NO: 7) |
| cg24084681 | First specific primer 08 | GGGTGGTTGATTTATGTAYGG (SEQ ID NO: 8) |
| cg06837426 | First specific primer 09 | AGATTGTGYGGTAGTAAGTTTTT (SEQ ID NO: 9) |
| cg00648301 | First specific primer 10 | GTTTGTTTGYGYGTTTG (SEQ ID NO: 10) |

The first specific primer pool was an equimolar mixture of the above-mentioned primers, and the Y base is a C/T degenerate base.

TABLE 4

| Nested Primer Pool | | |
|---|---|---|
| Target CpG sites | No. | Sequence |
| cg21646186 | Second specific primer 01 | ACATGGCTACGATCCGACTTGGAGTTTYGGGGYGYGTG (SEQ ID NO: 11) |
| cg19426625 | Second specific primer 02 | ACATGGCTACGATCCGACTTTTTTTGATATTGAAAATGTAATTGGTTTTT (SEQ ID NO: 12) |
| cg00960700 | Second specific primer 03 | ACATGGCTACGATCCGACTTGGTYTYGGTTGGYGTTTT (SEQ ID NO: 13) |
| cg06310157 | Second specific primer 04 | ACATGGCTACGATCCGACTTGGAGTATTTTATTTTTGTTGTTTATTATTATTTTT (SEQ ID NO: 14) |
| cg15025536 | Second specific primer 05 | ACATGGCTACGATCCGACTTGTTGAAGTGAGAATGTGATTATTAATTTTT (SEQ ID NO: 15) |
| cg12743416 | Second specific primer 06 | ACATGGCTACGATCCGACTTGTGTGTGTGTGTATTTATATATTTATATAAAA (SEQ ID NO: 16) |
| cg07382129 | Second specific primer 07 | ACATGGCTACGATCCGACTTTTAGAATTGAGATTAGAGAGGTAAGTAATG (SEQ ID NO: 17) |
| cg24084681 | Second specific primer 08 | ACATGGCTACGATCCGACTTGTTAAGTTGAAAAGTTGAATTTGTTTTT (SEQ ID NO: 18) |
| cg06837426 | Second specific primer 09 | ACATGGCTACGATCCGACTTYGGGTTGTTTTTGTATTTATTGTTG (SEQ ID NO: 19) |
| cg00648301 | Second specific primer 10 | ACATGGCTACGATCCGACTTGTATTTYGGTAATTTYGAGGTTG (SEQ ID NO: 20) |

The second specific primer pool is composed of the above-mentioned primers in an equimolar mixture, and the Y base is a C/T merged base.

TABLE 5

| Universal primers | |
|---|---|
| No. | Sequence |
| First universal primer | CGCTTGGCCTCCGACTT (SEQ ID NO: 21) |
| Second universal primer | /5Phos/#GAACGACATGGCTACGATCCGACTT (SEQ ID NO: 22) |
| Tagged primer | TGTGAGCCAAGGAGTTNNNNNNNNNNTTGTCTTCCTAAGACCGCTTGGC CTCCGACTT (SEQ ID NO: 23) |

In the above table, the N base is the barcode sequence on the MGI sequencing platform.

In the description of the present disclosure, the terms “first”, “second”, etc. are only used for descriptive purposes, and cannot be construed as indicating or implying relative importance or implicitly indicating the number of indicated technical features. Therefore, the features defined with “first” and “second” may explicitly or implicitly include at least one of the features. In the description of the present disclosure, “plurality” means at least two, such as two, three, etc., unless otherwise specifically defined.

In the present disclosure, unless otherwise clearly specified and limited, the terms “connected”, “connected”, “fixed” and other terms should be understood in a broad sense, for example, it can be a fixed connection, a detachable connection, or as one piece; mechanical connection or electrical connection or mutual communication; direct connection, or indirect connection through an intermediate medium; and internal communication between two components or mutual interaction between two components, unless otherwise specified. For those skilled in the art, the specific meaning of the above-mentioned terms in the present disclosure can be understood according to specific circumstances.

In the description of this specification, descriptions with reference to the terms “one embodiment”, “some embodiments”, “examples”, “specific examples”, or “some examples” etc. mean specific features, structure, materials or characteristics described in conjunction with the embodiment or example are included in at least one embodiment or example of the present disclosure. In this specification, the schematic representations of the above-mentioned terms are not necessarily directed to the same embodiment or example. Moreover, the described specific features, structures, materials or characteristics can be combined in any one or more embodiments or examples in a suitable manner. In addition, those skilled in the art can combine different embodiments or examples and the features of the different embodiments or examples described in this specification without contradicting each other.

Although the embodiments of the present disclosure have been illustrated and described above, it can be understood that the above-mentioned embodiments are exemplary and should not be construed as limiting the present disclosure. Those skilled in the art can make changes, modifications, replacements and modifications to the above-mentioned embodiments within the scope of the present disclosure.

What is claimed is:

1. A kit configured to construct a sequencing library based on a target region of a methylated DNA by a method for constructing a sequencing library based on a target region of a methylated DNA, the method comprising:

step 1 of obtaining a transformed DNA sample with universal sequence based on a methylated DNA sample by ligating a universal sequence to at least one end of the methylated DNA sample and treating the methylated DNA sample with bisulfite;

step 2 of performing, by using a first specific primer and a first universal primer, a first amplification on the transformed DNA sample with universal sequence to obtain a first amplification product, wherein the first specific primer is located upstream of the target region, the first universal primer is at least partially complementary to or at least partially overlaps the universal sequence, and the first universal primer is located downstream of the target region; and step 3 of performing, by using a second specific primer, a second universal primer and a tagged primer, a second amplification on the first amplification product to obtain a second amplification product and obtain the sequencing library, wherein the second specific primer, the second universal primer, and the tagged primer are set forth:

i: the second specific primer is located downstream of the first specific primer and upstream of the target region, the second universal primer at least partially overlaps a sequence of the second specific primer, the tagged primer contains a tag sequence, and the tagged primer partially overlaps a sequence of the first universal primer; or ii: the second specific primer is located downstream of the target region, the second universal primer at least partially overlaps a sequence of the first specific primer, the tagged primer contains a tag sequence, and the tagged primer partially overlaps a sequence of the second specific primer, wherein the first specific primer and the second specific primer are designed for only one strand of the DNA sample, the kit comprising:

a universal sequence to be ligated to at least one end of the methylated DNA sample, wherein the universal sequence is at least one selected from a sequencing adapter sequence or a modified sequencing adapter sequence, the sequencing adapter sequence being a known sequencing adapter sequence of a sequencing platform;

a tagged primer set forth as SEQ ID NO: 23;

a first universal primer set forth as SEQ ID NO: 21, wherein the first universal primer matches or overlaps at least a part of the universal sequence;

a second universal primer set forth as SEQ ID NO: 22;

a methylation detection reagent, wherein the methylation detection reagent is a bisulfite detection reagent;

a first specific primer comprising a sequence set forth as SEQ ID NO: 1 to SEQ ID NO: 10; and a second specific primer comprising a sequence set forth as SEQ ID NO: 11 to SEQ ID NO: 20, wherein the first specific primer and the second specific primer are designed for only one strand of a DNA sample.

2. The kit according to claim 1, wherein a 5'-end of the second specific primer at least partially overlaps a sequence of a 3'-end of the second universal primer, and a 3'-end of the tagged primer partially overlaps a sequence of a 5'-end of the first universal primer.

3. The kit according to claim 1, wherein a 5'-end of the second specific primer at least partially overlaps a sequence of a 3'-end of the tagged primer, and a 3'-end of the second universal primer partially overlaps a sequence of a 5'-end of the first specific primer.

4. The kit according to claim 1, wherein a 3'-end of a first sequencing primer comprises random bases, and a 5'-end of the first sequencing primer is the universal sequence.

5. The kit according to claim 4, wherein the 3'-end of the first sequencing primer comprises 6 to 12 random bases, and the random bases are A, T, or C.

6. The kit according to claim 4, wherein the universal sequence is a sequencing adapter sequence or a known sequence, wherein when the universal sequence is the sequencing adapter sequence, cytosine in the adapter sequence or the known sequence is methylated cytosine.

* * * * *